United States Patent
Giselbrecht et al.

(10) Patent No.: US 6,486,327 B1
(45) Date of Patent: Nov. 26, 2002

(54) METHOD FOR PRODUCING HYDROXYMETHYLPYRIDINES

(75) Inventors: Karlheinz Giselbrecht, Pasching (AT); Rudolf Hermanseder, Pennewang (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 250 days.

(21) Appl. No.: 10/129,189

(22) PCT Filed: Oct. 20, 2000

(86) PCT No.: PCT/EP00/10319

§ 371 (c)(1),
(2), (4) Date: May 2, 2002

(87) PCT Pub. No.: WO01/38307

PCT Pub. Date: May 31, 2001

(30) Foreign Application Priority Data

Nov. 26, 1999 (AT) .............................................. 2004/99

(51) Int. Cl.⁷ ...................... C07D 213/04; C07D 213/30
(52) U.S. Cl. ........................ 546/344; 546/249; 546/250; 546/344
(58) Field of Search ................................ 546/249, 250, 546/344

(56) References Cited

U.S. PATENT DOCUMENTS 3,637,721 A    1/1972  Pappas et al. .............. 260/297
3,952,026 A *  4/1976  Winter et al. ............. 260/347.8

OTHER PUBLICATIONS

Database Chemabs 'Online!'Chemical Abstracts Service, Columbus, Ohio, US: Amano et al., Database accession No. 127:293140 XP002158057—Abstract of JP 09–255654 (1997).
Queguiner et al., Bull. Soc. Chim. Fr., vol. 10, pp. 4117–4121 (1968).
White, Tetrahedron Letters. vol. 39, pp. 3587–3589 (1971).
Database Chemabs 'Online!'Chemical Abstracts Service, Columbus, Ohio, US: imanskaya et al., Database accession No. 103:215198 XP002158058—Abstract of SU 1,167,182 (1985).

* cited by examiner

*Primary Examiner*—Alan L. Rotman
*Assistant Examiner*—Janet L Coppins
(74) *Attorney, Agent, or Firm*—Wenderoth, Lind & Ponack, L.L.P.

(57) ABSTRACT

The invention relates to a method for producing hydroxymethylpyridines from the corresponding vinylpyridines by means of ozonisation in an alcohol as solvent and by means of hydrogenation of the peroxide-containing solution produced thereby, in the presence of a hydrogenation catalyst The hydrogenation solution is adjusted to a pH value of 10 to 14 by adding a base and the alcohol is distilled off and the desired hydroxymethylpyridine is isolated in high purity by extracting with an organic solvent and by means of subsequent distillative purification.

9 Claims, No Drawings

METHOD FOR PRODUCING HYDROXYMETHYLPYRIDINES

Hydroxymethylpyridines are valuable intermediates and find use, for example, in the synthesis of pharmaceuticals and agrochemicals, such as mefloquine hydrochloride or pineprofen.

The literature already describes a multiplicity of highly varied process variants for their preparation.

Chem. Abstr. Vol. 127; 293140, Vol. 106; 18373 or Vol. 103; 215195 discloses that 2- or 4-hydroxypyridine can be prepared in a yield of about 81 to 87% by catalytic reduction of the corresponding 2-cyano-pyridine.

Disadvantages of this process are the required high pressure and in particular the high price of the starting material.

A further possibility is the catalytic reduction of pyridinealdehydes using $H_2$ over Ba-promoted Cu chromite catalysts at 180 to 230° C. according to Chem. Abstr. Vol. 103: 215198 or the reduction with $NaBH_4$ according to Chem. Abstr. Vol. 93: 71487, and the latter says that the reactivity of the aldehydes toward reduction decreases in the order 2,6-pyridinecarboxaldehyde, 6-methyl-2-pyridinecarboxaldehyde, 4-pyridinecarboxaldehyde, 2-pyridinecarboxaldehyde and 3-pyridinecarboxaldehyde.

The disadvantage of these catalytic hydrogenations is that, owing to the deactivation of the catalyst used in each case, a large proportion of aldehyde is left unconverted, so that the end product is contaminated by large quantities of aldehyde.

A further disadvantage is the poor availability of the pyridinealdehyde.

Examples of other known variants are electro-chemical reduction of picolinic esters (e.g.: EP-A1-0 189 678) or the oxidation of alpha-picoline N-oxides sing trifluoroacetic anhydride (e.g.: Chem. Abstr. Vol. 122: 239462).

It is an object of the present invention to provide a process for preparing hydroxymethylpyridines which starts from easily accessible starting compounds and ensures a high purity of the desired end products, while allowing for a simple removal of interfering by-products.

The invention accordingly provides a process for preparing hydroxymethylpyridines which comprises
a) subjecting the corresponding vinylpyridine to ozonolysis in an alcohol solvent and hydrogenating the resulting peroxidic solution in the presence of a hydrogenation catalyst,
b) adjusting the hydrogenation solution by addition of a base to a pH of from 10 to 14 and distilling off the alcohol, and then
c) isolating the desired hydroxymethylpyridine in high purity by extraction with an organic solvent and subsequent distillative purification.

The process of the invention provides hydroxymethylpyridines (HMPs) in high purity. The process is particularly suitable for preparing a multiplicity of hydroxymethylpyridines such as 2-, 3- or 4-hydroxymethylpyridine, 6-methyl-2-hydroxy-methylpyridine, 2,6-di(hydroxymethyl)pyridine, etc. According to the invention, 2-, 3- or 4-hydroxymethylpyridine are preferably prepared, and 2-hydroxymethylpyridine is more preferably prepared.

The corresponding vinylpyridine serves as the starting compound, such as 2-, 3- or 4-vinylpyridine, 6-methyl-2-vinylpyridine and 2,6-divinylpyridine, which is converted in the first step by ozonolysis with subsequent catalytic hydrogenation.

The ozonolysis is carried out at temperatures of −80° C. to +20° C., preferably at −30° C. to +10° C. and more preferably at −25° C. to +5° C.

The corresponding vinylpyridine is reacted with maximally equivalent amount of ozone since the ozonolysis proceeds below the theoretical ozone consumption under the given process conditions. Stoichiometric quantities of the vinylpyridine used in each case are consumed. After the ozonization has ended, no measures are required to expel excess or unconverted ozone from the reaction mixture before hydrogenation.

The reaction with ozone takes place in an aliphatic $C_1$–$C_4$-alcohol, such as methanol, ethanol, butanol or propanol. Preferred solvents are methanol and ethanol, of which methanol is more preferred.

The catalytic hydrogenation of the ozonolysis products following the ozonization preferably takes place in highly dilute solution, the measure described below ensuring that during the entire hydrogenation a peroxide content of maximum 0.1 mol/l, preferably of maximum 0.05 mol/l and in particular of maximum 0.02 mol/l is set and maintained. To this end, a hydrogenation reactor is charged with a suspension of the catalyst in the alcoholic solvent used during ozonolysis and the solution resulting from the ozonization is continuously fed in by means of an adjustable metering apparatus. While the ozonization solution is added at the beginning and in the course of the hydrogenation care must of course be taken that the peroxide content in the hydrogenation reactor specified above not be exceeded owing to the introduced amount of the peroxidic ozonolysis products.

As a result of the low concentration of peroxidic ozonolysis solution in the reaction medium during the actual hydrogenation process caused by the continuous feeding in, a rapid reduction is ensured. In this way, poisoning of the catalyst and the loss of activity associated with it is prevented. Viewed overall, the continuous addition moreover allows a large quantity of ozonolysis products to be reduced in a comparatively small volume, which results in high concentrations of the corresponding HMP and savings in time and also in the costs of the distillative removal of the solvent.

Useful catalysts for the hydrogenations are suitable noble metal catalysts, which may be used in the form of powder catalysts with support materials or without support material. Palladium or platinum catalysts are preferably used. Examples of suitable support materials for powder catalysts include carbon, aluminum, silica gel or kieselguhr. Although yields are independent of the catalyst quantity used, in order to attain a sufficient hydrogenation rate it is recommended to use an initial charge of the catalysts mentioned in noble metal quantities of from 0.1 to 20% by weight, preferably from 1 to 15% by weight and more preferably from 5 to 10% by weight, based in each case on the total quantity of the ozonized vinylpyridines fed in per hour.

After the reduction has ended, the catalyst is separated from the reaction mixture.

In the process of the invention, equivalent quantities of hydrogen are consumed in reducing the ozonolysis products. The quantity of hydrogen which can be used in the hydrogenation ranges from one mole equivalent to a multiple molar excess. From 1.3 to 2.5 mol equivalents of hydrogen are preferably used, and from 1.8 to 2.2 mol equivalents are more preferably used.

The hydrogenation advantageously takes place under virtually atmospheric conditions. Virtually atmospheric conditions are to be understood as meaning pressures of from 1 to about 3 bar, as is customary in industrial practice to prevent ingress of air into the hydrogenation reactor. In this way, the reduction of the ozonolysis products is very simple to practice in industry. However, it is also possible to perform the hydrogenation under a pressure of up to 20 bar and thereby increase the rate of hydrogenation. The reduction is exothermic and in a preferred embodiment is conducted at temperatures of from 20 to 60° C., in particular at temperatures in the range from 35 to 50° C.

After the hydrogenation, the reaction solution is separated from the catalyst and preferably concentrated, for example using a rotary evaporator, and the alcohol used as solvent is distilled off as an alcohol-water mixture. The formaldehyde formed as a by-product of the conversion of the vinylpyridines to the corresponding HMP is also removed substantially from the reaction solution. In order to recycle the alcohol, formaldehyde can be converted, for example by means of an acidic ion exchanger to formaldehyde dialkyl acetal, separated distillatively from the alcohol and then burnt.

After the concentration, the remaining reaction solution is then admixed with a suitable base, such as NaOH, KOH, CaOH, etc., and preferably with NaOH in combination with aqueous ammonia, preferably in 25% strength, so that a pH value of from 10 to 14, preferably from 11 to 13 is set. During this exothermic procedure, the by-produced alkyl picolinate is hydrolyzed and the remaining formaldehyde converted to urotropine.

However, the reaction solution remaining after the concentration can also be admixed only with one suitable base, such as NaOH, KOH, CaOH, etc., preferably 20 to 50% strength NaOH without aqueous ammonia, again until a pH of from 10 to 14, preferably from 11 to 13, is attained, and heated to from 60 to 110° C., preferably from 75 to 85° C. In this case, the by-produced alkyl picolinate is again hydrolyzed and the remaining formaldehyde converted to formate and methanol.

In a preferred embodiment, the hydrogenation solution can be sucked into a basic initial charge, such as an NaOH, KOH or CaOH initial charge, preferably into a 20 to 50% strength NaOH initial charge, using a rotary evaporator, and alcohol and water are simultaneously distilled off, which again results in the hydrolysis of the by-produced alkyl picolinate and the conversion of the remaining formaldehyde into formate and methanol, but scarcely any formaldehyde can be detected in the distillate. The pH here is also from 10 to 14.

In all three cases, after a water content of from 30 to 70%, preferably from 40 to 60% and more preferably from 45 to 55%, has been attained in strongly basic bottom product, extraction is performed using an organic solvent at a temperature of from 15 to 50° C., preferably from 20 to 45° C. Suitable solvents include customary extractants that are inert under the reaction conditions, such as toluene, ether, etc.

Ethers are preferably used, more preferably methyl t-butyl ether (MTBE).

In order to ensure complete extraction, multiple extractions may be necessary depending on the solvent used and the solubility of the HMPs in the solvent. The collected organic phases are then concentrated and the residue is distilled at from 10 to 200 mbar, preferably at from 30 to 100 mbar, more preferably at from 40 to 60 mbar, and at the maximum necessary liquid phase temperature.

During the distillation, about 5% is preferably separated off as the first cut and about 5% as the bottom product.

An advantage of the work-up of the invention is that in particular in the preferred embodiment no formaldehyde has to be burnt and in the event of any incomplete hydrogenation the corresponding pyridinealdehyde formed by the ozonolysis is converted to a substantial extent (over 70%) by the formaldehyde present in excess by a crossed Cannizzaro reaction to the corresponding hydroxymethylpyridine.

A further advantage is that the by-products resulting from the ozonolysis-reduction mechanism, such as pyridine-carboxylic acid, pyridine-carboxylic esters, pyridinealdehyde and formaldehyde can be easily removed and the end products can be obtained in yields of up to 80% and a purity of above 99.5% by weight.

EXAMPLE 1

Preparation of 2-Hydroxymethylpyridine

A 0.5 mol solution of 2-vinylpyridine in methanol was ozoninized at −15° C. using ozone in a concentration of 50 g/m$^3$ h and the solution obtained in this way fed via a feed vessel into a hydrogenation reactor, which had been initially charged with a suspension of 5% Pd/C catalyst in methanol and filled with hydrogen, at such a rate that the peroxide content did not exceed 0.02 mol/l. Hydrogenation was continued with vigorous stirring and hydrogen addition until a negative peroxide test was obtained, and the temperature was held at 45° C. After the hydrogenation had ended, the catalyst was separated off.

Step b)

The hydrogenation solution obtained in this way was continuously sucked into an initial 40% sodium hydroxide charge with a pH value above 12 and methanol/water was simultaneously distilled off at 80° C. and under slightly reduced pressure. During this 3.5-hour process, the methyl picolinate was hydrolyzed and the formaldehyde converted to sodium formate and methanol. Almost no formaldehyde could be detected in the distillate by oxime titration (less than 50 mg/l of methanol).

Step c)

Once a water content of about 50% had been obtained in the strongly basic bottom product, extraction was performed at room temperature using MTBE, and 40 g of 2-hydroxymethylpyridine were soluble in a liter of MTBE. In order to ensure complete extraction, 10 extractions were necessary. About 1.7 kg of bottom product from the extraction (about 65% water content) was separated off per kg of 2-vinylpyridine used.

The collected organic phases were concentrated on a rotary evaporator at 60° C. and under slightly reduced pressure and the residue distilled at a maximum of the necessary liquid phase temperature of 140° C. and 50 mbar. During the distillation, about 5%, which comprised ethylpyridine, water, etc., was separated off as first cut and 5% as bottom product.

The purity of the colorless main fraction was >99% and the formaldehyde content <100 ppm.

The yield of 2-hydroxymethylpyridine was 67% based on the 2-vinylpyridine used.

EXAMPLE 2

Ozonolysis and hydrogenation of Example 1 were repeated.

Step b)

The hydrogenation solution obtained in this way was continuously sucked into a rotary evaporator and methanol/water/formaldehyde were simultaneously distilled off at 80° C. and under slightly reduced pressure. During this 3.5-hour process, 90% of the formaldehyde was distilled off.

Methyl picolinate was then hydrolyzed by addition of 40% sodium hydroxide in excess and the remaining formaldehyde converted to sodium formate and methanol at 80° C. within 2 hours.

Step c)

Once a water content of about 50% had been obtained in the strongly basic bottom product, extraction was performed at room temperature using MTBE, and 40 g of 2-hydroxymethylpyridine were soluble in a liter of MTBE. In order to ensure complete extraction, 10 extractions were necessary.

The collected organic phases were concentrated on a rotary evaporator at 60° C. and under slightly reduced pressure, and the residue distilled at a maximum of the necessary liquid phase temperature of 150° C. and 50 mbar. During the distillation, about 5%, which comprised ethylpyridine, water, etc., was separated off as first cut and 5% as bottom product.

The purity of the colorless main fraction was >99% and the formaldehyde content <100 ppm.

The yield of 2-hydroxymethylpyridine was 76% based on the 2-vinylpyridine used.

What is claimed is:

1. A process for preparing hydroxymethylpyridines which comprises
    a) subjecting the corresponding vinylpyridine to ozonolysis in an alcohol solvent and hydrogenating the resulting peroxidic solution in the presence of a hydrogenation catalyst,
    b) adjusting the hydrogenation solution by addition of a base to a pH of from 10 to 14 and distilling off the alcohol, and then
    c) isolating the desired hydroxymethylpyridine in high purity by extraction with an organic solvent and subsequent distillative purification.

2. The process according to claim 1, wherein 2-, 3- or 4-hydroxymethylpyridine, 6-methyl-2-hydroxymethylpyridine or 2,6-di(hydroxymethyl)pyridine are prepared.

3. The process according to claim 1, wherein the alcohol used is an aliphatic $C_1$–$C_4$-alcohol.

4. The process according to claim 1, wherein the hydrogenation is carried out at from 1 to 3 bar.

5. The process according to claim 1, wherein the catalyst is separated off after the hydrogenation, the reaction solution is concentrated by distilling off an alcohol-water mixture and the pH is set to 10 to 14 by addition of a base.

6. The process according to claim 1 wherein the catalyst is separated off after the hydrogenation, the reaction solution is introduced into a basic initial charge and water and alcohol are simultaneously distilled off.

7. The process according to claim 1, wherein the water content of the strongly basic bottom product obtained in step c) by distilling off the alcohol and adding a base is set from 30 to 70% and the resulting hydroxymethylpyridine is then extracted from the bottom product using an organic solvent that is inert under the reaction conditions at a temperature of from 15 to 50° C.

8. The process as claimed in claim 1, wherein the organic solvent used for extraction in step c) is ether.

9. The process as claimed in claim 1, wherein the distillative purification of the organic phases obtained by extraction is carried out at from 10 to 200 mbar.

* * * * *